United States Patent
Konishi et al.

(10) Patent No.: US 10,646,386 B2
(45) Date of Patent: May 12, 2020

(54) METHOD FOR RECOVERING PULP FIBER FROM USED HYGIENE PRODUCT

(71) Applicant: UNICHARM CORPORATION, Ehime (JP)

(72) Inventors: Takayoshi Konishi, Kagawa (JP); Toshio Hiraoka, Kagawa (JP); Noritomo Kameda, Kagawa (JP); Hideaki Ichiura, Kochi (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/064,073

(22) PCT Filed: Oct. 24, 2016

(86) PCT No.: PCT/JP2016/081491
§ 371 (c)(1),
(2) Date: Jun. 20, 2018

(87) PCT Pub. No.: WO2017/110234
PCT Pub. Date: Jun. 29, 2017

(65) Prior Publication Data
US 2019/0000698 A1 Jan. 3, 2019

(30) Foreign Application Priority Data
Dec. 25, 2015 (JP) .................. 2015-255231

(51) Int. Cl.
*A61F 13/84* (2006.01)
*A61L 2/04* (2006.01)
(Continued)

(52) U.S. Cl.
CPC .............. *A61F 13/84* (2013.01); *A61F 13/15* (2013.01); *A61L 2/04* (2013.01); *A61L 2/18* (2013.01);
(Continued)

(58) Field of Classification Search
None
See application file for complete search history.

(56) References Cited

U.S. PATENT DOCUMENTS

| 5,429,311 A | 7/1995 | Cina et al. |
| 6,319,361 B1 * | 11/2001 | Smith .................. D21C 9/005 |
| | | 162/146 |

(Continued)

FOREIGN PATENT DOCUMENTS

| CN | 1149262 A | 5/1997 |
| CN | 104411881 A | 3/2015 |

(Continued)

OTHER PUBLICATIONS

ISR for PCT/JP2016/081491 dated Jan. 24, 2017, 2pp.

*Primary Examiner* — Jacob T Minskey
(74) *Attorney, Agent, or Firm* — Hauptman Ham, LLP

(57) ABSTRACT

Provided is a method for efficiently recovering pulp fiber from used hygiene products that include pulp fiber and a polymer absorbent. This method is characterized by including a step for introducing the used hygiene product into a treatment tank in which an aqueous solution with ozone dissolved therein has been introduced, and a step for treating the used hygiene product while infusing water into the treatment tank at a first flow rate, extracting the aqueous solution from the treatment tank at a second flow rate and introducing a gas containing ozone into the aqueous solution in the treatment tank, thereby decomposing the polymer absorbent, lowering the molecular weight thereof, and making the same dissolvable.

14 Claims, 3 Drawing Sheets

(51) Int. Cl.
*A61L 2/18* (2006.01)
*A61L 11/00* (2006.01)
*C08J 11/16* (2006.01)
*D21C 5/02* (2006.01)
*D21H 11/14* (2006.01)
*B09B 3/00* (2006.01)
*A61F 13/15* (2006.01)
*D21B 1/32* (2006.01)

(52) U.S. Cl.
CPC ............... *A61L 11/00* (2013.01); *B09B 3/00* (2013.01); *B09B 3/0016* (2013.01); *C08J 11/16* (2013.01); *D21B 1/322* (2013.01); *D21C 5/02* (2013.01); *D21H 11/14* (2013.01)

(56) References Cited

U.S. PATENT DOCUMENTS

| | | | |
|---|---|---|---|
| 2011/0268606 | A1 | 11/2011 | Glazer et al. |
| 2015/0291762 | A1* | 10/2015 | Watanabe ......... A61F 13/15707 428/401 |
| 2016/0237617 | A1* | 8/2016 | Yamaguchi ............. D21C 5/02 |

FOREIGN PATENT DOCUMENTS

| | | | | |
|---|---|---|---|---|
| JP | S46-4210 | Y1 | | 1/1971 |
| JP | H4-317785 | A | | 11/1992 |
| JP | H6-269746 | A | | 9/1994 |
| JP | 2001-47023 | A | | 2/2001 |
| JP | 2002-292304 | A | | 10/2002 |
| JP | 2014-217835 | A | | 11/2014 |
| JP | 6009721 | B1 * | 10/2016 | ............ F21V 19/004 |
| WO | 2014/168179 | A1 | | 10/2014 |

* cited by examiner

METHOD FOR RECOVERING PULP FIBER FROM USED HYGIENE PRODUCT

RELATED APPLICATIONS

The present application is a National Phase of International Application No. PCT/JP2016/081491 filed Oct. 24, 2016 and claims priority to Japanese Application No. 2015-255231, filed on Dec. 25, 2015.

FIELD

The present invention relates to a method of recovering pulp fibers from a used hygiene product. More specifically, the present invention relates to a method of recovering pulp fibers from a used hygiene product which includes pulp fibers and a polymer absorbent material, such as a used disposable paper diaper, etc.

BACKGROUND

There has been an attempt to recycle hygiene products such as used disposable paper diapers, etc. In order to recycle used hygiene products, normally, the used hygiene products are decomposed in water, and components of the hygiene products are separated and recovered. However, the polymer absorbent material (hereinbelow, also referred to as "SAP") included in the hygiene products increases the mass thereof by absorbing moisture and loses liquidity due to transforming into a gel state, whereby lowers the treating capacity of the treatment apparatus.

Accordingly, Japanese Unexamined Patent Publication No. 2014-217835 proposed a method of decomposing the SAP in the used paper diaper, making the SAP dissolvable and removing the SAP by immersing the used paper diaper in an acidic ozone water with pH of 3 or lower.

PRIOR ART DOCUMENTS

Patent Documents

[Patent Document 1] Japanese Unexamined Patent Publication No. 2014-21783

DISCLOSURE OF THE INVENTION

Problems to be Solved by the Invention

However, the method of Japanese Unexamined Patent Publication No. 2014-217835 requires addition of acid in order to use the acidic ozone water with pH of 3 or lower, which further requires treatment of discharging acidic waste water. Further, there may be cases in which an oxide is generated by ozone depending on the types of the added acid, and problems of safety may occur.

Still further, when the decomposing of SAP proceeds, the ozone is consumed also for decomposing SAP of which the molecular weight is lowered so as to be water-soluble. As a result, there has been a problem in which the decomposing efficiency is lowered, and it takes time to finish decomposing SAP.

Means for Solving the Problems

The present inventors found out that it is possible to efficiently decompose SAP without using acidic water by supplying a certain amount of fresh water in a tank which is in the process of ozone treatment and at the same time pulling out the same amount of treatment water so as not to make the SAP concentration high in the treatment tank after decomposing SAP, whereby completed the present invention.

That is, the present invention is a method of recovering pulp fibers from a used hygiene product which includes pulp fibers and a polymer absorbent material, comprising:
a step of introducing the used hygiene product into a treatment tank with an ozone dissolved aqueous solution; and
a step of treating the used hygiene product, decomposing the polymer absorbent material, lowering a molecular weight of the polymer absorbent material and making the polymer absorbent material dissolvable, while injecting water into the treatment tank by a first flow rate, discharging the aqueous solution from the treatment tank by a second flow rate, and introducing an ozone containing gas into the aqueous solution inside the treatment tank.

The present invention includes the following aspects.

[1] A method of recovering pulp fibers from a used hygiene product which includes pulp fibers and a polymer absorbent material, comprising:
a step of introducing the used hygiene product into a treatment tank with an ozone dissolved aqueous solution; and
a step of treating the used hygiene product, decomposing the polymer absorbent material, lowering a molecular weight of the polymer absorbent material and making the polymer absorbent material dissolvable, while injecting water into the treatment tank by a first flow rate, discharging the aqueous solution from the treatment tank by a second flow rate, and introducing an ozone containing gas into the aqueous solution inside the treatment tank.

[2] The method according to [1], wherein the first flow rate $R_1$ (unit: L/minute) and a volume V (unit: L) of the aqueous solution inside the treatment tank satisfy formula (1):

$$0.05 \leq R_1/V \leq 0.2 \tag{1}$$

[3] The method according to [1] or [2], wherein an ozone concentration of the aqueous solution is 1 to 30 mass ppm.

[4] The method according to any one of [1] to [3], wherein an ozone concentration of the ozone containing gas is 40 to 60 g/m³.

[5] The method according to any one of [1] to [4], wherein a flow rate $R_O$ (unit: L/minute) of the ozone containing gas and a volume V (unit: L) of the aqueous solution inside the treatment tank satisfy formula (2):

$$0.5 \leq R_O/V \leq 1.25 \tag{2}$$

[6] The method according to any one of [1] to [5], wherein a product of an ozone concentration (mass ppm) of the aqueous solution and a time (minute) of the step of treating the used hygiene product, decomposing the polymer absorbent material, lowering the molecular weight of the polymer absorbent material and making the polymer absorbent material dissolvable is 100 to 6000 mass ppm·minute.

[7] The method according to any one of [1] to [6], wherein a volume V (unit: L) of the aqueous solution inside the treatment tank and a mass W (unit: kg) of the used hygiene product satisfy formula (3):

$$3 \leq V/W \leq 50 \tag{3}$$

[8] The method according to any one of [1] to [7], further comprising a step of extracting, from the treatment tank, a residue of the hygiene product from which the polymer absorbent material is removed.

[9] The method according to any one of [1] to [8], further comprising a step of washing a residue of the hygiene product and decomposing the residue of the hygiene product into components, by stirring the residue of the hygiene product from which the polymer absorbent material is removed in an aqueous solution or in water, including a disinfectant.

[10] The method according to [9], wherein
the disinfectant is sodium hypochlorite, chlorine dioxide, acidic electrolyzed water, ozone water, acidic ozone water, or ozone water including organic acid.

[11] The method according to [9] or [10], further comprising a step of separating the pulp fibers from the decomposed residue of the hygiene product.

[12] The method according to [11], further comprising a step of washing the separated pulp fibers.

[13] The method according to [12], further comprising a step of dehydrating the washed pulp fibers.

[14] The method according to any one of [1] to [13], further comprising a step of drying the pulp fibers, wherein
the dried pulp fibers are made to have a moisture percentage of 5 to 13% by the step of drying the pulp fibers.

[15] The method according to [14], wherein
a temperature at which the pulp fibers are dried is 100 to 200° C.

[16] The method according to any one of [1] to [15], further comprising a step of separating and recovering a plastic material.

[17] The method according to any one of [1] to [16], wherein
the second flow rate is the same as the first flow rate.

[18] The method according to any one of [1] to [17], wherein
the hygiene product is a disposable paper diaper.

Effects of the Invention

According to the present invention, a polymer absorbent material can be efficiently decomposed by ozone without using acidic water, and pulp fibers can be efficiently recovered from a used hygiene product which includes pulp fibers and a polymer absorbent material.

MODE FOR CARRYING OUT THE INVENTION

Figure 1:
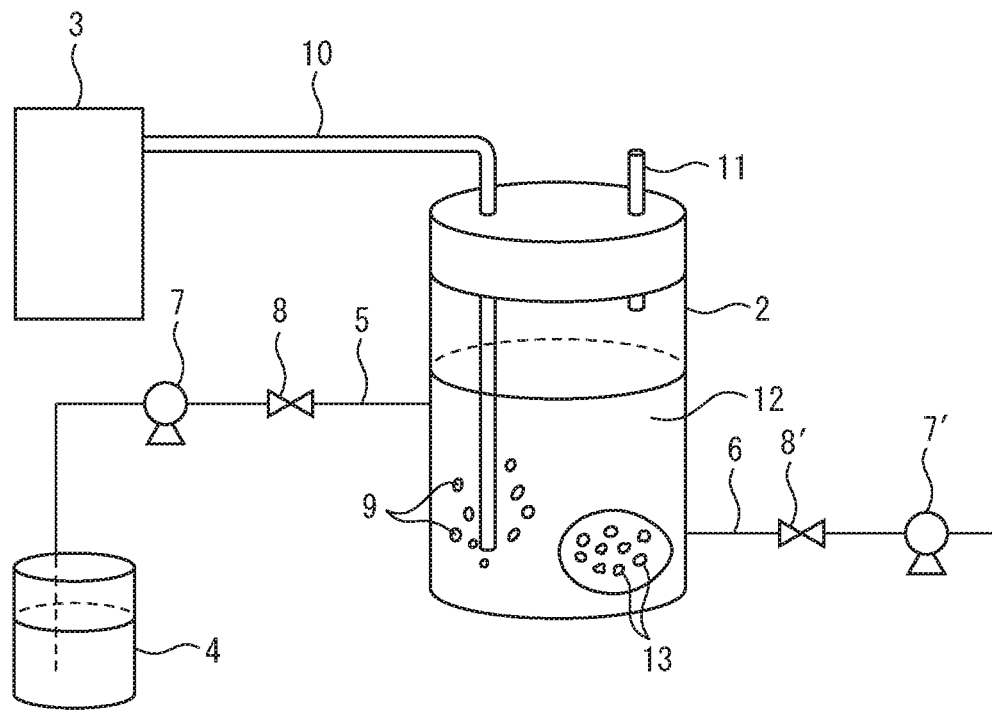
FIG. 1 is a schematic diagram of an ozone water treatment apparatus used in the embodiment.

The present invention is a method of recovering pulp fibers from a used hygiene product which includes pulp fibers and a polymer absorbent material.

A hygiene product is not particularly limited as long as the hygiene product includes pulp fibers and a polymer absorbent material, and as the hygiene product, a disposable paper diaper, a urine removal pad, a sanitary napkin, a panty liner, etc., may be mentioned.

The used hygiene product is referred to as a hygiene product which has absorbed body fluid such as manure, menstrual blood, etc.

As the pulp fibers, although not particularly limited, fluff-like pulp fibers, chemical pulp fibers, etc., may be mentioned.

The polymer absorbent material is also referred to as a super absorbent polymer (SAP), which has a three dimensional network structure in which water soluble polymers are moderately crosslinked, is essentially water insoluble although absorbing several hundred times to one thousand times of water, and has a function of not releasing water once absorbed even when some pressure is applied. As the polymer absorbent material, for example, starch type, acrylic acid type, or amino acid type, particulate or fibrous polymers may be mentioned.

The method of the present invention includes:
a step of introducing the used hygiene product into a treatment tank with an ozone dissolved aqueous solution; and
a step of treating the used hygiene product, decomposing the polymer absorbent material, lowering a molecular weight of the polymer absorbent material and making the polymer absorbent material dissolvable, while injecting water into the treatment tank by a first flow rate, discharging the aqueous solution from the treatment tank by a second flow rate, and introducing an ozone containing gas into the aqueous solution inside the treatment tank.

The method of the present invention further includes, as needed:
a step of extracting, from the treatment tank, a residue of the hygiene product from which the polymer absorbent material is removed,
a step of washing a residue of the hygiene product and decomposing the residue of the hygiene product into components, by stirring the residue of the hygiene product from which the polymer absorbent material is removed in an aqueous solution or in water, including a disinfectant,
a step of separating the pulp fibers from the decomposed residue of the hygiene product,
a step of washing the separated pulp fibers,
a step of dehydrating the washed pulp fibers, and
a step of drying the pulp fibers.

The first step is the step of introducing the used hygiene product into a treatment tank with an ozone dissolved aqueous solution (hereinbelow, also simply referred to as "the introducing step").

The "ozone dissolved aqueous solution" used in this step may be prepared, for example by introducing the ozone containing gas generated by an ozone generating device (for example, ozone water exposure test machine ED-OWX-2 manufactured by EcoDesign, Inc., or ozone generating device OS-25V manufactured by Mitsubishi Electric Corporation, etc.) into water so that the ozone is dissolved in water.

The ozone concentration in the aqueous solution is not particularly limited as long as the polymer absorbent material can be decomposed, however, the ozone concentration is preferably 1 to 30 mass ppm, more preferably 2 to 20 mass ppm, and even more preferably 3 to 10 mass ppm. When the ozone concentration is too low, there may be cases in which the polymer absorbent material cannot be completely solubilized, and the polymer absorbent material may remain in the recovered pulp fibers. Conversely, when the ozone concentration is too high, since the oxidizing power also increases, there may be cases in which the pulp fibers are damaged, and further, problems of safety may occur.

The amount of the aqueous solution inside the treatment tank is not particularly limited as long as the polymer absorbent material can be decomposed, however, it is preferable that the volume V (unit: L) of the aqueous solution inside the treatment tank and the mass W (unit: kg) of the used hygiene product satisfy formula (3):

$$3 \leq V/W \leq 50 \tag{3}.$$

The volume V (unit: L) of the aqueous solution inside the treatment tank and the mass W (unit: kg) of the used hygiene product more preferably satisfy $5 \leq V/W \leq 40$, and even more preferably satisfy $8 \leq V/W \leq 30$. When V/W is too small, there may be cases in which the polymer absorbent material cannot be completely solubilized, and the polymer absorbent material may remain in the recovered pulp fibers. Conversely, when V/W is too large, the manufacturing cost may be increased.

The next step is the step of treating the used hygiene product, decomposing the polymer absorbent material, lowering a molecular weight of the polymer absorbent material and making the polymer absorbent material dissolvable, while injecting water into the treatment tank by a first flow rate, discharging the aqueous solution from the treatment tank by a second flow rate, and introducing an ozone containing gas into the aqueous solution inside the treatment tank (hereinbelow, also simply referred to as "the treating step").

In this step, the polymer absorbent material is decomposed, the molecular weight thereof is lowered, and the polymer absorbent material is made dissolvable. The state in which the polymer absorbent material is decomposed, the molecular weight thereof is lowered, and the polymer absorbent material is made dissolvable is referred to the state of capable of passing through a screen mesh of 2 mm. That is, in this step, the polymer absorbent material is decomposed to the extent that the polymer absorbent material passes through a screen mesh of 2 mm.

It is preferable that a screen mesh of 2 mm is provided at the discharging port of the treatment tank. The polymer absorbent material decomposed to the extent that the polymer absorbent material passes through a screen mesh of 2 mm passes through the screen mesh of 2 mm, and is discharged along with the aqueous solution.

The first flow rate $R_1$ (unit: L/minute) and the volume V (unit: L) of the aqueous solution inside the treatment tank preferably satisfy formula (1):

$$0.05 \leq R_1/V \leq 0.2 \tag{1}.$$

The first flow rate $R_1$ (unit: L/minute) and the volume V (unit: L) of the aqueous solution inside the treatment tank more preferably satisfy $0.05 \leq R_1/V \leq 0.15$, and even more preferably satisfy $0.075 \leq R_1/V \leq 0.10$. When $R_1/V$ is too small, the COD concentration in the treatment water is increased and the polymer absorbent material cannot be completely solubilized, whereas when $R_1/V$ is too large, the time it takes to dissolve ozone in water is shortened, and it is difficult to maintain high ozone concentration, whereby the polymer absorbent material cannot be completely solubilized.

The first flow rate (hereinbelow, also referred to as "the introducing flow rate") the second flow rate (hereinbelow, also referred to as "the discharging flow rate") are preferably the same. By setting the first flow rate and the second flow rate the same, the amount of the aqueous solution inside the treatment tank can be maintained constant. As long as the amount of the aqueous solution inside the treatment tank can be maintained substantially constant, in other words, as long as the amount of the aqueous solution inside the treatment tank does not significantly increase or decrease, the first flow rate and the second flow rate may fluctuate over time. The first flow rate and the second flow rate do not necessarily be completely identical at all times, and may be substantially the same on average over time. Substantially the same is referred to as the state in which the difference is within 5%.

The treating step is performed while introducing an ozone containing gas into the aqueous solution inside the treatment tank.

The ozone concentration of the ozone containing gas is preferably 40 to 60 g/m³, more preferably 40 to 50 g/m³, and even more preferably 42.5 to 45 g/m³. When the concentration is too low, the polymer absorbent material cannot be completely solubilized, whereas when the concentration is too high, it may cause damage to the pulp fibers, decrease in safety, and increase in manufacturing cost.

The flow rate $R_O$ (unit: L/minute) of the ozone containing gas and the volume V (unit: L) of the aqueous solution inside the treatment tank preferably satisfy formula (2):

$$0.5 \leq R_O/V \leq 1.25 \tag{2}.$$

The flow rate $R_O$ (unit: L/minute) of the ozone containing gas and the volume V (unit: L) of the aqueous solution inside the treatment tank more preferably satisfy $0.5 \leq R_O/V \leq 1.0$, and even more preferably satisfy $0.5 \leq R_O/V \leq 0.75$. When $R_O/V$ is too small, the polymer absorbent material cannot be completely solubilized, whereas when $R_O/V$ is too large, it may cause damage to the pulp fibers, decrease in safety, and increase in manufacturing cost.

The time of the treating step is not particularly limited as long as the polymer absorbent material can be decomposed. The time of the treating step can be short when the ozone concentration of the aqueous solution is high, and it takes a long time when the ozone concentration of the aqueous solution is low.

The product of the ozone concentration (mass ppm) of the aqueous solution and the time (minute) of the treating step (hereinbelow, also referred to as "CT value") is preferably 100 to 6000 mass ppm·minute, more preferably 200 to 4800 mass ppm·minute, and even more preferably 300 to 3600 mass ppm·minute. When the CT value is too small, there may be cases in which the polymer absorbent material cannot be completely solubilized, and the polymer absorbent material may remain in the recovered pulp fibers. Conversely, when the CT value is too large, it may cause damage to the pulp fibers, decrease in safety, and increase in manufacturing cost.

In the treating step, during the treatment, the content of the treatment tank may or may not be stirred. Further, a weak flow may be generated in the aqueous solution, by letting the bubbles of the ozone containing gas move upward. The temperature of the aqueous solution is not particularly limited as long as the polymer absorbent material can be decomposed. The aqueous solution may be heated, or kept at room temperature.

In the treating step, the polymer absorbent material is affected by the oxidative decomposition reaction of ozone, the three dimensional network structure of the polymer absorbent material collapses, the polymer absorbent material loses water retention property, the molecular weight thereof is lowered, and is made to be dissolvable. The polymer absorbent material with higher liquidity is dissolved in an aqueous solution. The decomposed polymer absorbent material which has dissolved in the aqueous solution is discharged along with the aqueous solution, whereby solid particles of the polymer absorbent material do not remain in the residue of the used hygiene product. Further, the hot melt adhesive agent which is used for joining, etc., of the hygiene product is also oxidized and deteriorated by ozone, whereby the joining strength between components of the hygiene product is weakened. Still further, in this step, the used hygiene product is subjected to the primary disinfection by a bactericidal action of ozone.

The method of the present invention may further include the step of extracting, from the treatment tank, the residue of the hygiene product from which the polymer absorbent material is removed (hereinbelow, also simply referred to as "the extracting step"). The method of extracting the residue of the hygiene product from the treatment tank is not particularly limited, and for example, the residue of the hygiene product in the aqueous solution may be scooped up with a net of 2 mm mesh. Conversely, after discharging the aqueous solution from the treatment tank through a screen mesh of 2 mm, the residue of the hygiene product may be recovered from the treatment tank.

The method of the present invention may further include the step of washing the residue of the hygiene product and decomposing the residue of the hygiene product into components, by stirring the residue of the hygiene product from which the polymer absorbent material is removed in an aqueous solution or in water, including a disinfectant (hereinbelow, also simply referred to as "the washing·decomposing step").

The disinfectant does not necessarily be included in the water to be used in the washing·decomposing step, and further, an aqueous solution including a disinfectant may be used. The disinfectant is not particularly limited, and for example, sodium hypochlorite, chlorine dioxide, acidic electrolyzed water, ozone water, acidic ozone water, ozone water including organic acid, etc., may be mentioned, and in particular, sodium hypochlorite is preferable from the viewpoint of economy and versatility.

In a case in which the aqueous solution including a disinfectant is used, the disinfectant concentration in the aqueous solution including a disinfectant is not particularly limited as long as the effect of the disinfection is demonstrated, and the disinfectant concentration is preferably 10 to 300 mass ppm, more preferably 30 to 280 mass ppm, and even more preferably 50 to 250 mass ppm. When the concentration is too low, sufficient effect by the disinfection cannot be obtained, and there may be cases in which bacteria, etc., remains in the recovered pulp fibers. Conversely, when the concentration is too high, not only it causes waste of disinfectant, but also there may be cases in which the pulp fibers are damaged, and problems of safety occur.

The stirring in the washing·decomposing step is not particularly limited as long as the residue of the hygiene product is washed and decomposed into components, and for example, the stirring may be performed by using a washing machine. The conditions of the stirring is also not particularly limited as long as the residue of the hygiene product is washed and decomposed into components, and for example, the stirring time is preferably 5 to 60 minutes, more preferably 10 to 50 minutes, and even more preferably 20 to 40 minutes.

In the washing·decomposing step, the residue of the hygiene product from which the polymer absorbent material is removed is washed, and further, the hygiene product is decomposed into pieces of components. In the above described treating step, since the hot melt adhesive agent which is used for joining, etc., of the hygiene product is oxidized and deteriorated by ozone, and the joining strength between components of the hygiene product is weakened, in the washing·decomposing step, the hygiene product can be easily decomposed into components by stirring. When an aqueous solution including a disinfectant is used, disinfection by the disinfectant is also performed.

After the washing·decomposing step, the step of separating the pulp fibers from the decomposed residue of the hygiene product (hereinbelow, also simply referred to as "the pulp fibers separating step") may be provided.

The method of separating the pulp fibers from the decomposed residue of the hygiene product, although not limited, may for example be performed by scooping up the pulp fibers floating in the liquid which includes the decomposed residue of the hygiene product.

After the pulp fibers separating step, the step of washing the separated pulp fibers (hereinbelow, referred to as "the pulp fibers washing step") may be provided.

The method of washing the separated pulp fibers, although not limited, may for example be performed by placing the separated pulp fibers into a mesh bag and rinse the separated pulp fibers with water. The rinse washing may be performed in a batch mode, a semi-batch mode, or a circulation mode. In a case of performing the rinse washing in a batch mode, for example, rinsing by using a washing machine may be performed.

The condition of the washing is not particularly limited as long as substances other than the pulp fibers are sufficiently removed, and for example, the washing time is preferably 3 to 60 minutes, more preferably 5 to 50 minutes, and even more preferably 10 to 40 minutes. In a case of performing the rinse washing in a batch mode, the amount of water to be used, with respect to 100 parts by mass (absolute dry mass) of pulp fibers, is preferably 500 to 5000 parts by mass, more preferably 800 to 4000 parts by mass, and even more preferably 1000 to 3000 parts by mass.

After the pulp fibers washing step, the step of dehydrating the washed pulp fibers (hereinbelow, referred to as "the pulp fibers dehydrating step") may be provided.

The method of dehydrating the washed pulp fibers, although not limited, may for example be performed by dehydrating the washed pulp fibers placed in a mesh bag and by a dehydrating machine.

The conditions of the dehydration is not particularly limited as long as the moisture percentage can be decreased to the target value, and for example, the dehydration time is preferably 1 to 10 minutes, more preferably 2 to 8 minutes, and even more preferably 3 to 6 minutes.

The pulp fibers washing step and the pulp fibers dehydrating step may be performed once each, or may be alternately repeated for a plurality of times.

The method of the present invention may include the step of drying the pulp fibers (hereinbelow, referred to as "the pulp fibers drying step").

The pulp fibers drying step is performed at least after the pulp fibers separating step is finished. Preferably, the pulp fibers drying step is performed after the pulp fibers washing step or the pulp fibers dehydrating step.

The method of drying the pulp fibers, although not limited, may for example be performed by using a drying machine such as a hot air dryer, etc.

The conditions of the drying is not particularly limited as long as the pulp fibers are sufficiently dried, and for example, the drying temperature is preferably 100 to 200° C., more preferably 110 to 180° C., and even more preferably 120 to 160° C. The drying time is preferably 10 to 120 minutes, more preferably 20 to 80 minutes, and even more preferably 30 to 60 minutes.

The moisture percentage of the pulp fibers after drying is preferably 5 to 13%, more preferably 6 to 12%, and even more preferably 7 to 11%. When the moisture percentage is too low, there may be cases in which the hydrogen bonding is too strong and the pulp fibers are to be too stiff, and conversely, when the moisture percentage is too high, there may be cases in which molds, etc., occur.

The moisture percentage of the pulp fibers is measured as follows. Incidentally, this measurement is performed under the atmosphere of 20° C.±1° C.

(1) The mass A (g) of the container (a container without a lid) to place the measurement target sample is measured.

(2) Approximately 5 g of the measurement target sample is prepared, and is placed in the container the mass of which is measured in (1), and the mass B (g) of the container in which the sample is placed is measured.

(3) The container in which the sample is placed is left in an oven for 2 hours, the temperature of which being set to 105° C.±3° C.

(4) The container in which the sample is placed is removed out from the oven and is left in a desiccator (drying agent: the one containing colored silica gel) for 30 minutes.

(5) The container in which the sample is placed is removed out from the desiccator, and the mass C (g) is measured.

(6) The moisture percentage (%) is measured by the following formula.

Moisture percentage (%)=$(B-C)/(C-A) \times 100$

The method of the present invention may further include the step of separating and recovering a plastic material (hereinbelow, referred to as "the plastic material separating and recovering step"). The plastic material is referred to as a nonwoven fabric material, a film material, and an elastomer material, etc. The plastic material separating and recovering step may be performed after the above described washing·decomposing step, in parallel with the pulp fibers separating step. The plastic material separating and recovering step may include a washing step, a dehydrating step and a drying step similar to the above described pulp fibers washing step, the pulp fibers dehydrating step and the pulp fibers drying step. The recovered plastic material may for example be subjected to RPF conversion treatment so as to be used as a solid fuel.

In the treatment of a batch mode, the polymer absorbent material (SAP) with high molecular weight is decomposed, and the molecular weight thereof is lowered, so as to be water soluble, and numerous low molecular weight substances are dissolved in the aqueous solution, whereby the ozone is largely consumed by the decomposition of the low molecular weight substances, and it is difficult to increase the decomposition efficiency, however, on the other hand, by always replacing a certain amount of the aqueous solution with water, since the concentration of the water soluble low molecular weight SAP is lowered, and ozone can be consumed mainly for the decomposition of high molecular weight SAP, it is possible to increase the decomposition efficiency. Accordingly, even without a treatment in acid (organic acid) water such as citric acid, etc., it is possible to efficiently decompose and remove SAP.

By the method of the present invention, the polymer absorbent material is decomposed by ozone so as to lower the molecular weight thereof and to be dissolvable, whereby the polymer absorbent material is dissolved in the aqueous solution and can be discharged along with the aqueous solution. Accordingly, the polymer absorbent material does not remain between the pulp fibers, and pulp fibers with an ash content conforming to the hygienic material standards can be recovered efficiently. According to the method of the present invention, since metal salts such as lime, etc., are not used for deactivating water absorption of the polymer absorbent material, an ash content which derives from the deactivated polymer absorbent material (Ca cross-linked body) is not detected. Further, according to the method of the present invention, since the polymer absorbent material is made to be dissolvable, the liquidity inside the treatment tank is not lost by the swollen polymer absorbent material, and decrease in the treating capacity of the treatment apparatus does not occur. Still further, according to the method of the present invention, the decomposition and dissolving of the polymer absorbent material is possible by a relatively low concentration of dissolved ozone concentration of 1 to 30 ppm, and it is possible to treat the polymer absorbent material safely. Still further, according to the method of the present invention, in the ozone water immersion step, since the hot melt adhesive agent which is used for joining, etc., of the hygiene product is oxidized and deteriorated by ozone water, and the joining strength between components of the hygiene product is weakened, in the washing·decomposing step, the hygiene product can be easily decomposed into components by stirring.

Still further, according to the method of the present invention, in the first stage, the recovered diapers are immersed in the ozone dissolved aqueous solution, and the polymer absorbent material is oxidized and decomposed by the oxidizing power of ozone, whereby the polymer absorbent material in a swollen particle state is made into an aqueous solution, and further, the primary disinfection is performed, and in the next washing step, the stain which could not be removed is removed and additional disinfection (the secondary disinfection) is performed by the ozone water, and subsequently, the pulp fibers are separated from other materials (the plastic material, etc.), heating and drying are performed respectively, and drying and heat disinfection (the tertiary disinfection) are performed. By dissolving and removing the polymer absorbent material at the primary state, the recycle is made possible with simple steps, and by using the ozone water for dissolving the polymer absorbent material, three times of disinfection in total are made possible, which ensures high level of safety.

EXAMPLES

Preparation of the Polymer Absorbent Material Samples 1.5 g of the polymer absorbent material (super absorbent polymer "AQUA KEEP" SA60 manufactured by Sumitomo Seika Chemicals Co., Ltd.) was placed in a bag made of a PE mesh sheet (PE200, Sanplatec Co., Ltd., opening of 102 µm). The bag which contained the polymer absorbent material was immersed in 80 mL of 0.9% physiological saline for 15 minutes and the absorption treatment was performed. Subsequently, the bag was pulled out, was left on a drainer net for 15 minutes so as to perform draining, and wet weight measurement was performed. The absorbed polymer absorbent material was defined as Na-SAP.

1.5 g of the polymer absorbent material (super absorbent polymer "AQUA KEEP" SA60 manufactured by Sumitomo Seika Chemicals Co., Ltd.) was placed in a bag made of a PE mesh sheet (PE200, Sanplatec Co., Ltd., opening of 102 μm). The bag which contained the polymer absorbent material was immersed in 80 mL of artificial urine for 15 minutes and the absorption treatment was performed. Subsequently, the bag was pulled out, was left on a drainer net for 15 minutes so as to perform draining, and wet weight measurement was performed. The artificial urine was prepared by dissolving 20 g of urea, 8 g of sodium chloride, 0.8 g of magnesium sulfate heptahydrate and 0.3 g of calcium chloride dehydrate in 1000 mL of distilled water. The absorbed polymer absorbent material was defined as U-SAP.

Ozone Water Treatment Apparatus

The apparatus used for the ozone water treatment is shown in FIG. 1. The ozone water treatment apparatus 1 includes the treatment tank 2 which is configured by a 2 L glass container, the ozone generating device 3, and the water tank 4. The treatment tank 2 is attached with the water injecting pipe 5 and the water discharging pipe 6. The water tank 4 and the treatment tank 2 are connected through the water injecting pipe 5, and the tubing pump 7 and the two way cock 8 are provided in the water injecting pipe 5. The two way cock 8' and the tubing pump 7' are also provided in the water discharging pipe 6. The ozone containing gas 9 which is generated at the ozone generating device 3 is supplied to the treatment tank 2 through the gas introducing pipe 10. 11 shows the gas discharging pipe, 12 shows the ozone dissolved aqueous solution (hereinbelow, also referred to as "ozone water"), and 13 shows the polymer absorbent material sample. As the ozone generating device 3, the ozone water exposure test machine ED-OWX-2 manufactured by EcoDesign, Inc. was used.

Wet Mass Residual Rate

The wet mass residual rate of the polymer absorbent material samples was calculated by the following formula.

Wet mass residual rate (%)=$W/W_0 \times 100$

W: the wet mass of the polymer absorbent material sample after the treatment
$W_0$: the wet mass of the polymer absorbent material sample before the treatment Measurement of Ozone Concentration in the Aqueous Solution 85 mL of the ozone dissolved aqueous solution was put into a 100 mL measuring cylinder in which approximately 0.15 g of potassium iodide and 5 mL of 10% citric acid solution had been put. After the reaction, the mixture was transferred to a 200 mL Erlenmeyer flask. Further, a starch solution was added thereto, was colored to purple, and thereafter, while stirring the mixture until the mixture turned colorless by 0.01 mol/L sodium thiosulfate, titration was performed.

The ozone concentration in the aqueous solution was calculated by the following formula based on the titration value.

The ozone concentration in the aqueous solution (mass ppm)=the amount of 0.01 mol/L sodium thiosulfate required for the titration (mL)×0.24× 0.85 (mL)

Example 1

Figure 2:
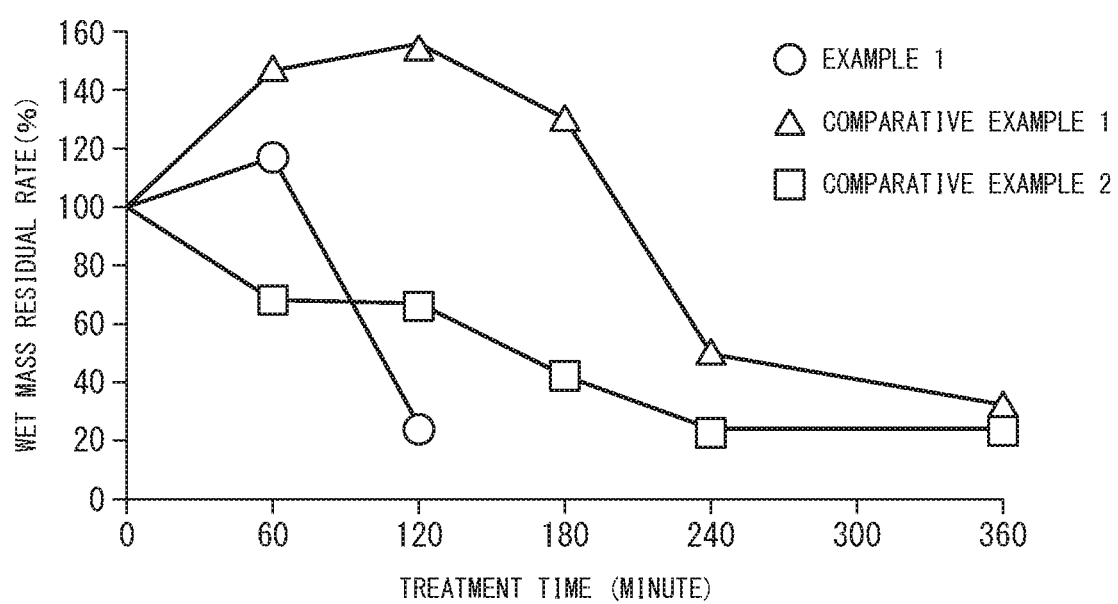
FIG. 2 is a diagram which shows the relationship between the treatment time and the wet mass residual rate in a Na-SAP ozone water treatment.
Figure 4:
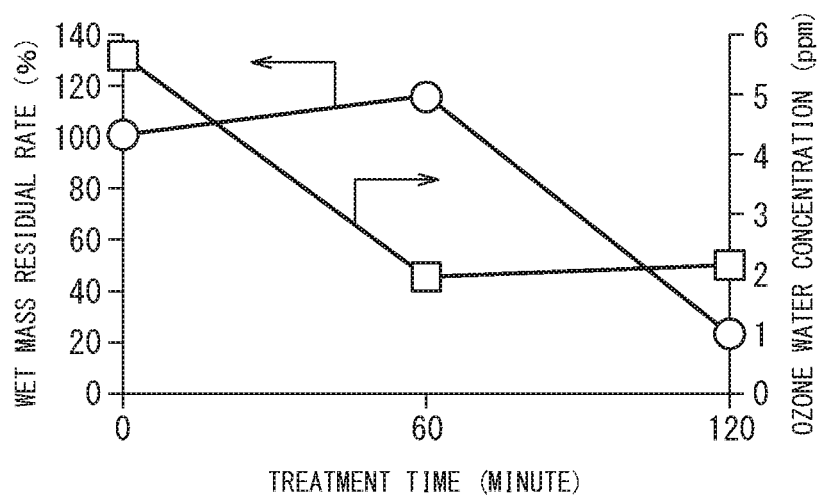
FIG. 4 is a diagram which shows the relationship between the wet mass residual rate and the ozone water concentration in Example 1.

By using the ozone generating device 3, 2 L of ozone water 12 with an ozone concentration of approximately 5 ppm was prepared in the treatment tank 2. As the prepared polymer absorbent material sample 13, Na-SAP was immersed in the ozone water 12 for 5 minutes in the treatment tank 2. After 5 minutes, the tubing pumps 7, 7' were operated and introducing of water was started with the flow rate of 0.2 to 0.3 L/min, and at the same time, discharging of water from the glass container was started with the flow rate of 0.2 to 0.3 L/min. During the treatment, the ozone containing gas 9 with the ozone gas concentration of approximately 40 g/m³ was kept being supplied with the flow rate of 1.0 L/min from the ozone generating device 3, and the generation of the ozone water was continued in the treatment tank 2. The treatment was performed until the polymer absorbent material sample after treatment was dried at 105° C. for 12 hours and thereafter the measured dry mass was too small that the measurement was no longer possible. After the treatment, the wet mass measurement of the polymer absorbent material sample 13 was performed. The relationship between the treatment time and the wet mass residual rate is shown in FIG. 2. The relationship between the wet mass residual rate and the ozone water concentration is shown in FIG. 4.

Comparative Example 1

Figure 6:
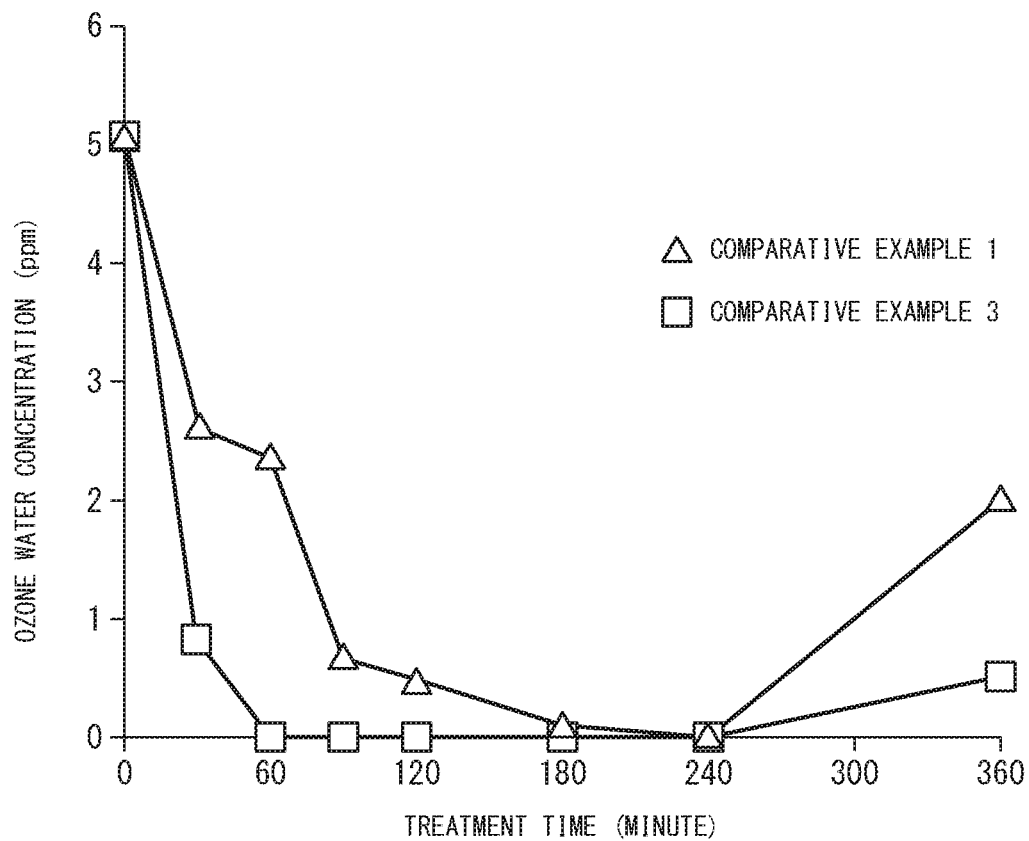
FIG. 6 is a diagram which shows the relationship between the treatment time and the ozone water concentration in Comparative Examples 1 and 3.

The same process was performed as in Example 1, except for not operating the tubing pumps 7, 7'. The relationship between the treatment time and the wet mass residual rate is shown in FIG. 2. The relationship between the treatment time and the ozone water concentration is shown in FIG. 6.

Comparative Example 2

The same process was performed as in Comparative Example 1, except for dissolving citric acid with the concentration of 1 mass % in the ozone water. The relationship between the treatment time and the wet mass residual rate is shown in FIG. 2.

Example 2

Figure 3:
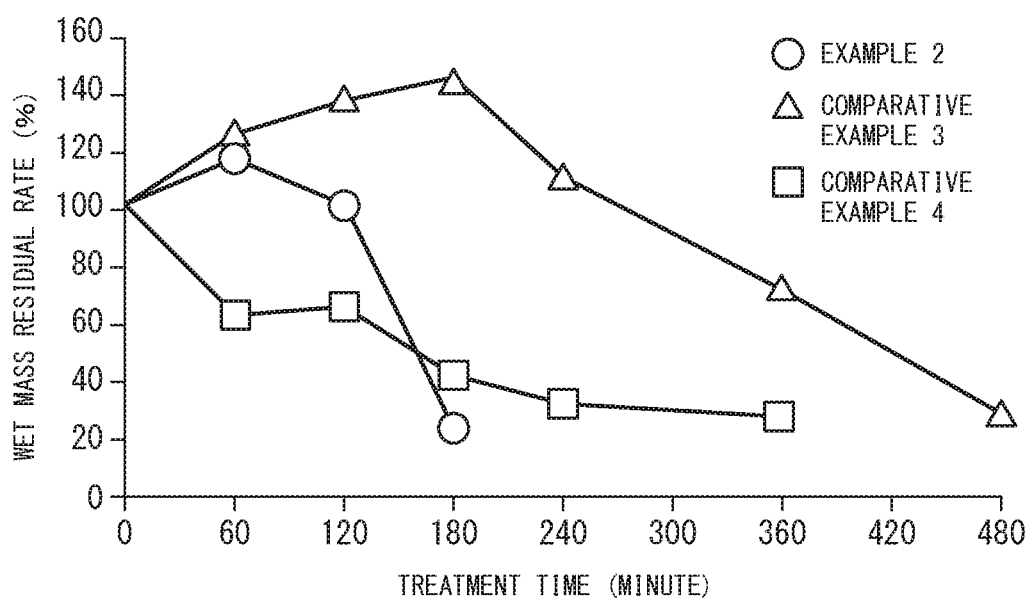
FIG. 3 is a diagram which shows the relationship between the treatment time and the wet mass residual rate in a U-SAP ozone water treatment.
Figure 5:
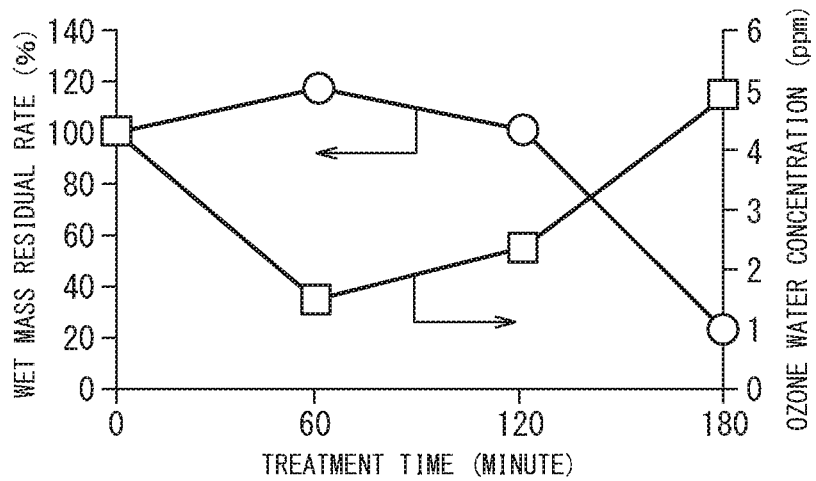
FIG. 5 is a diagram which shows the relationship between the wet mass residual rate and the ozone water concentration in Example 2.

The same process was performed as in Example 1, except for changing Na-SAP to U-SAP. The relationship between the treatment time and the wet mass residual rate is shown in FIG. 3. The relationship between the wet mass residual rate and the ozone water concentration is shown in FIG. 5.

Comparative Example 3

The same process was performed as in Example 2, except for not operating the tubing pumps 7, 7'. The relationship between the treatment time and the wet mass residual rate is shown in FIG. 4. The relationship between the treatment time and the ozone water concentration is shown in FIG. 6.

Comparative Example 4

The same process was performed as in Comparative Example 3, except for dissolving citric acid with the concentration of 1 mass % in the ozone water. The relationship between the treatment time and the wet mass residual rate is shown in FIG. 4.

With regard to the ozone water treatment of Na-SAP, as shown in FIG. 2, the treatment of the polymer absorbent material sample was able to be finished in as short as 2 hours in Example 1. This means that the polymer absorbent material sample was decomposed in 2 hours. Accordingly, it can be understood that the polymer absorbent material can be efficiently decomposed by the circulation mode rather than the batch mode.

With regard to the ozone water treatment of U-SAP, as shown in FIG. 3, the treatment of the polymer absorbent material sample was able to be finished in as short as 3 hours in Example 2. This means that the polymer absorbent material sample was decomposed in 3 hours. Accordingly, it can be understood that the polymer absorbent material can be efficiently decomposed by the circulation mode rather than the batch mode.

With regard to the relationship between the ozone water concentration and the wet mass residual rate, in the case of the batch mode, as the wet mass residual rate decreased, the ozone water concentration significantly decreased (until 0 ppm) (refer to FIG. 6). As shown in FIGS. 4 and 5, in the method of the present invention, high ozone water concentration was able to be maintained compared to the batch mode. Accordingly, it can be conceived that high decomposition efficiency was able to be obtained compared to the batch mode.

INDUSTRIAL APPLICABILITY

The pulp fibers which are recovered by the method of the present invention can be preferably used for manufacturing hygiene products again.

The invention claimed is:

1. A method of recovering pulp fibers from a used hygiene product which includes pulp fibers and a polymer absorbent material, the method comprising:
    introducing the used hygiene product into a treatment tank with an ozone dissolved aqueous solution; and
    decomposing the polymer absorbent material to lower a molecular weight of the polymer absorbent material and make the polymer absorbent material dissolvable,
    wherein said decomposing comprises treating the used hygiene product under a circulation mode by
        injecting water into the treatment tank by a first flow rate,
        discharging the aqueous solution from the treatment tank by a second flow rate, and
        introducing an ozone containing gas into the aqueous solution inside the treatment tank, wherein
    a product of an ozone concentration (mass ppm) of the aqueous solution and a time (minute) of the treating the used hygiene product is 100 to 6000 mass ppm·minute.

2. The method according to claim 1, wherein the first flow rate $R_1$ (unit: L/minute) and a volume V (unit: L) of the aqueous solution inside the treatment tank satisfy formula (1):
$$0.05 \leq R_1/V \leq 0.2 \qquad (1).$$

3. The method according to claim 1, wherein an ozone concentration of the aqueous solution is 1 to 30 mass ppm.

4. The method according to claim 1, wherein an ozone concentration of the ozone containing gas is 40 to 60 g/m$^3$.

5. The method according to claim 1, wherein a flow rate $R_O$ (unit: L/minute) of the ozone containing gas and a volume V (unit: L) of the aqueous solution inside the treatment tank satisfy formula (2):
$$0.5 \leq R_O/V \leq 1.25 \qquad (2).$$

6. The method according to claim 1, wherein a volume V (unit: L) of the aqueous solution inside the treatment tank and a mass W (unit: kg) of the used hygiene product satisfy formula (3):
$$3 \leq V/W \leq 50 \qquad (3).$$

7. The method according to claim 1, further comprising: extracting, from the treatment tank, a residue of the hygiene product from which the polymer absorbent material is removed.

8. The method according to claim 1, further comprising: washing a residue of the hygiene product and decomposing the residue of the hygiene product into components, by stirring the residue of the hygiene product from which the polymer absorbent material is removed in an aqueous solution or in water, including a disinfectant.

9. The method according to claim 8, wherein the disinfectant is sodium hypochlorite, chlorine dioxide, acidic electrolyzed water, ozone water, acidic ozone water, or ozone water including organic acid.

10. The method according to claim 8, further comprising: separating the pulp fibers from the decomposed residue of the hygiene product.

11. The method according to claim 1, further comprising: drying the pulp fibers until the dried pulp fibers have a moisture percentage of 5 to 13%.

12. The method according to claim 11, wherein a temperature at which the pulp fibers are dried in said drying is 100 to 200° C.

13. The method according to claim 1, further comprising: separating and recovering a plastic material.

14. The method according to claim 1, wherein the second flow rate is the same as the first flow rate.

* * * * *